United States Patent

Spielberg

[19]

[11] Patent Number: 6,048,306
[45] Date of Patent: Apr. 11, 2000

[54] NON-INVASIVE DUAL ACTING UROLOGICAL PRESS FOR THE PREVENTION OF FEMALE INCONTINENCE

[75] Inventor: Theodore E. Spielberg, 10 Pinewood Cir., Wellesley, Mass. 02181

[73] Assignee: Theodore E. Spielberg, Wellesley, Mass.

[21] Appl. No.: 09/134,851

[22] Filed: Aug. 14, 1998

[51] Int. Cl.[7] ...................................................... A61F 5/48
[52] U.S. Cl. ............................................. 600/29; 128/885
[58] Field of Search ........................... 128/885, DIG. 25, 128/830, 834, 845; 600/29, 30, 32

[56] References Cited

U.S. PATENT DOCUMENTS

| | | | |
|---|---|---|---|
| 3,554,184 | 1/1971 | Habib | 600/29 |
| 3,705,575 | 12/1972 | Edwards | 600/29 |
| 4,428,365 | 1/1984 | Hakky . | |
| 4,875,898 | 10/1989 | Eakin | 604/331 |
| 4,920,986 | 5/1990 | Biswas | 128/885 |
| 4,942,886 | 7/1990 | Timmons | 128/885 |
| 5,012,822 | 5/1991 | Schwarz | 128/885 |
| 5,036,867 | 8/1991 | Biswas | 128/885 |
| 5,082,006 | 1/1992 | Jonasson | 128/885 |
| 5,097,848 | 3/1992 | Schwarz | 128/885 |
| 5,123,428 | 6/1992 | Schwarz | 128/885 |
| 5,386,836 | 2/1995 | Biswas | 128/885 |
| 5,417,226 | 5/1995 | Juma | 128/885 |
| 5,453,278 | 9/1995 | Chan et al. | 128/885 |
| 5,483,976 | 1/1996 | McLaughlin et al. | 424/422 |
| 5,509,427 | 4/1996 | Simon et al. | 128/885 |
| 5,513,659 | 5/1996 | Buuck et al. | 128/885 |
| 5,513,660 | 5/1996 | Simon et al. | 128/885 |
| 5,520,606 | 5/1996 | Schoolman et al. | 600/31 |
| 5,603,685 | 2/1997 | Tutrone, Jr. | 600/29 |

*Primary Examiner*—Cary O'Connor
*Attorney, Agent, or Firm*—Cesari & McKenna

[57] ABSTRACT

A urethral press seals the female bladder against the inadvertent discharge of urine into the urethra. The press comprises a resilient curved band, preferably U-shaped, having a first arm for insertion into the vagina and a second arm extending exteriorly of the vagina along the pubic area to provide a force to compress the bladder and the contiguous urethral walls to thereby seal the bladder.

8 Claims, 1 Drawing Sheet

NON-INVASIVE DUAL ACTING UROLOGICAL PRESS FOR THE PREVENTION OF FEMALE INCONTINENCE

BACKGROUND OF THE INVENTION

A. Field of the Invention

The invention relates to devices for the prevention of incontinence in females.

B. Prior Art

Incontinence of urine is a common problem in mature women. With aging, hormonal changes and the consequences of childbirth, there is a loosening of tissues resulting in the loss of the normal angle at the bladder outlet to the urethra known as the urethrovesical (UV) junction. This junction or angle normally serves to support the sphincter at the bladder outlet that contains urine. Since urination depends on relaxing the sphincter, a loss in the UV junction angle results in permanent partial relaxation and urinary dribbling. The dribbling is further aggravated by sudden increases in abdominal pressure caused by sneezing, coughing, and laughing, and is known as "stress incontinence."

In order to correct this problem, several surgical procedures have been designed. Although helpful, they are not always appropriate, and they are not universally successful. Therefore, various devices have been used to deal with this problem.

Among these devices are pads that soak up the urine and must be changed at frequent intervals, urethral caps, held in by adhesives to attempt to block urethral leakage, and an invasive urethral catheter device, anchored by an inflatable balloon to plug the urethra.

The pads are cumbersome and require frequent changing, the caps are only partially effective and depend on a potentially irritating adhesive, and the catheter balloon can cause urethral irritation and infection as it is an invasive device.

Wholly intra-vaginal devices have been proposed for addressing the problem if incontinence. These have the disadvantage that they create rectal pressure, and thus discomfort. Additionally, they are often difficult to insert and remove and are difficult to properly place. Further, intra-vaginal device with rings must be sized to the specific patient, and cannot be used at all for post-hysterectomy patients.

SUMMARY OF THE INVENTION

Therefore, the object of this invention is to effectively prevent urinary incontinence of women by correcting the pathophysiological state that caused the problem, with a small comfortable device, without adhesives, that is non-invasive and easy to use, and has a dual mode of action for increased security.

A U-shaped The invention comprises a U-shaped having a first arm for vaginal insertion and a second arm that extends externally along the pubic area. The tension inherent in the curvilinear portion of the U-shaped press, serves to keep the device in place. The first or interior arm preferably terminates in a an enlarged area such as a "wing" that is wedged in the anterior vaginal vault under the pubic bone and which prevents its extrusion from the vagina unless specifically removed. The second or exterior arm also preferably terminates in an enlarged area for pressing against the pubic area.

The two ends of the tensioned press device need to be pulled apart for insertion and removal. The vaginal portion of the device presses upwardly and anteriorly on the anterior vaginal wall and therefore on the urethra and bladder, serving to restore the normal UV angle. Furthermore, the apex of the inner surface of the device is compressed against the urethral opening to additionally prevent urine leakage by providing a seal. Additionally, a disposable, deformable pad may be inserted over the urethral opening to be compressed by the device for sanitary and comfort considerations, as well as to further secure the seal in the manner of a gasket. The device may preferentially be constructed in plastic, metal, and/or latex in various combinations, and may be made in various sizes.

DRAWINGS

The invention description below refers to the accompanying drawings, of which:

FIG. 1 is a view in perspective of a preferred embodiment of the urological press of the present invention; and FIG. 2 is a side sectional view of a patient showing the press of the invention anchored in the vaginal canal in order to eliminate incontinence.

DETAILED DESCRIPTION OF AN ILLUSTRATIVE EMBODIMENT

Figure 1:
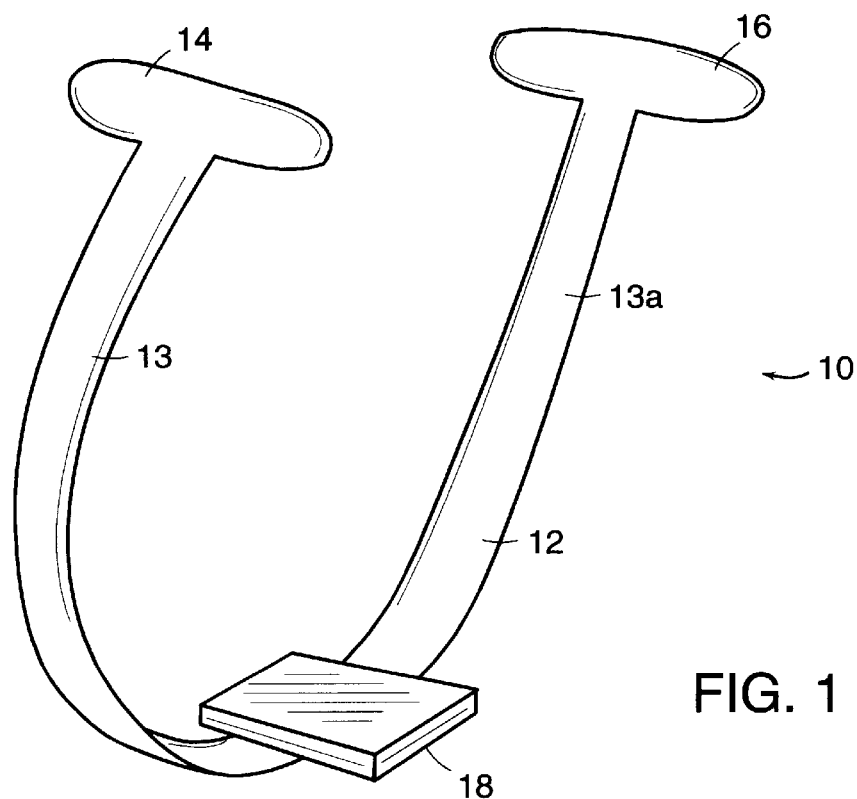

In FIG. 1, a preferred form of urological press 10 in accordance with the present invention is formed from a flattened band 12 having first and second arms 13 and 13a, respectively, and having end wings 14 and 16 at the ends of the arms. The band is generally U-shaped, and is formed of resilient material providing a restoring force when the wings are released after being momentarily forced apart. For this purpose, the press is preferably made of a resilient plastic, or of spring steel coated with a protective plastic. A disposable, liquid-absorbent pad 18 is removably secured to the band 12 by means of adhesive, by a snap fastener or other such means. The pad is disposed on the band 12 in such a position as to be located opposite the entrance to the urethra when the press is inserted into the vagina as shown in FIG. 2.

Figure 2:
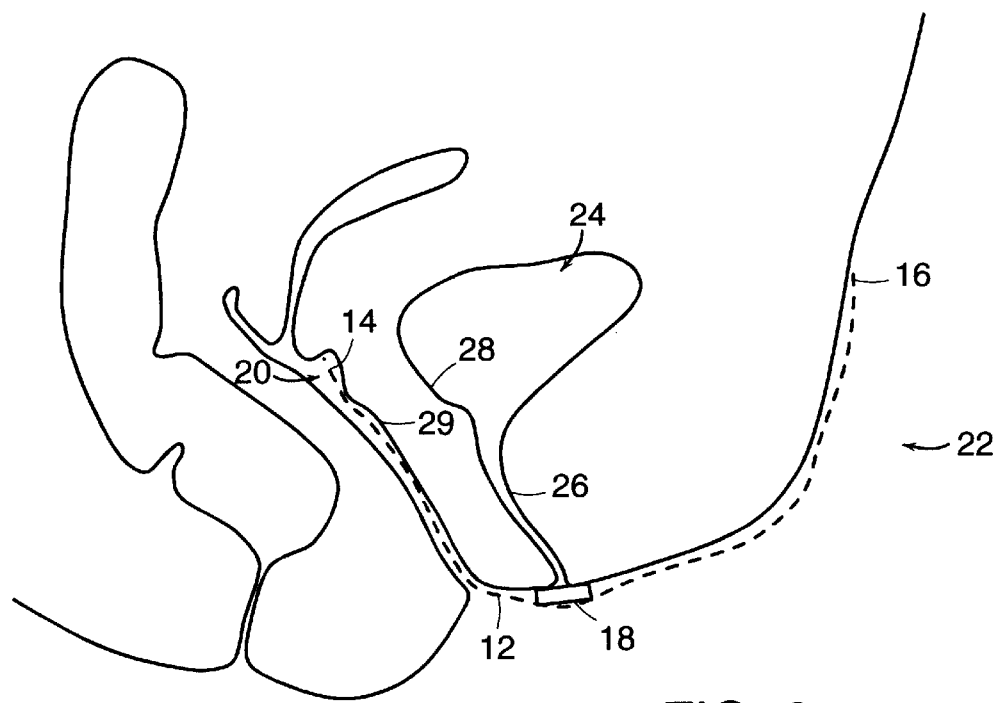

In FIG. 2, the press 10 (depicted by dotted lines for purposes of illustration) is shown inserted in the vagina 20 of a patient 22. In particular, wing 14 is positioned in the anterior vaginal vault behind the bladder 24 and presses against the posterior wall of the bladder and urethra. The band 12 extends down the vagina and generally conforms to the pubic area. It terminates in the wing 16 which presses against the upper portion of the pubic area.

The bladder 24 discharges its contents through the urethra 26. As a result of increasing age, childbirth, illness or other events, the anterior wall 28 of the bladder often loses its resilience and increasingly relaxes. In consequence, the contents of the bladder increasingly leak into the urethra and are involuntarily discharged. The present invention provides a force that effectively restores the proper angle of the urethral bladder junction by pressing the bladder anteriorly and superiorly through the anterior wall 29 of the vagina (posterior wall of the bladder) to thereby compress the opening from the bladder into the urethra, thereby preventing inadvertent leakage from the bladder.

In particular, in the position shown in FIG. 2, the band 10 is deformed from its natural position by insertion in the vagina. This deformation creates a tensional force in the press which seeks to move the two ends of the press back together. Because the pubic bone restricts movement of the wing 16, the wing 14 moves anteriorly, toward the wing 16, thereby pressing on the posterior urethro-vessicle wall and returns the urethro-vessicle angle from an abnormal relaxed condition, allowing urethral leakage, to its normal acuity, preventing or restricting such leakage. The pad 18 absorbs whatever minor leakage there may be.

The curvature of the band 12 provides the force required to compress the posterior urethral bladder wall. The wing 14 helps to anchor the arm 13 in the vagina; additionally, the wings 14 and 16 provide enlarged surface area for pressing against the body parts. The band 12 is preferably on the order of one-quarter inch wide and one-sixteenth inch thick. The wings 14 and 16 are preferably on the order of one inch in width and one-half to one inch in height to provide the desired surface area for application of restoring force to the urethral-bladder wall. The wing 14 may be rounded or otherwise shaped to conform to the vaginal anatomy. The pad 18 is advantageously of limited dimension, e.g., on the order of a square inch. Its capacity for liquid retention need only be minimal, since the press itself, apart from the pad, is the primary instrument for suppression of urethral leakage.

The press is provided in a variety of sizes to accommodate the range of anatomical variations. However, it may also advantageously be custom fitted and/or molded to the particular anatomy in specific cases. In particular, it may be contoured to the particular shape of the vaginal canal of a patient, to thereby increase not only patient comfort, but also the degree of sealing of the urethral canal when the press is worn by the patient.

The press of the present invention is small, light-weight, and easy to insert and remove. It is inconspicuous, and non-invasive, and has no intraurethral or surgical component.

It will be understood that changes may be made in the foregoing preferred embodiment of the invention, without departing from either the spirit or the scope thereof. For example, while the arms have been shown as relatively straight, it will be understood that they may be curved simply or in a compound manner over part or all of their extent in order to vary the force-loading along their length and thus along the length of their contact with the urethro-vessicle wall and pubis in order to accommodate more particularly to specific anatomy.

What is claimed is:

1. A press for sealing the female bladder against unintended discharge of urine into the urethra, comprising a one-piece continuous resilient self-retaining curved band having a first arm for insertion into the vagina and a second arm for extending exteriorly of said vagina along the pubic area to and compressible there against solely by the spring force of said band to provide a force for compressing the bladder and contiguous urethra superiorly and anteriorly through the anterior vaginal wall to thereby seal the bladder.

2. A press according to claim 1 in which said first arm terminates in a wing of enlarged surface area for anchoring said arm in said vagina.

3. A press according to claim 1 in which said second arm terminates in a wing of enlarged surface area for pressing against the pubic area.

4. A press according to claim 1 in which said band includes means for receiving a pad on a surface thereof for further protection against inadvertent leakage from the urethra.

5. A press according to claim 1 in which said band is generally U-shaped.

6. A press according to claim 5 in which said band is formed of a flexible plastic material providing a restoring force when said arms are forced apart.

7. A press according to claim 5 in which said band is formed of a plastic-coated spring steel.

8. A press according to claim 1 or 5 in which at least said first arm is specifically contoured to the vaginal anatomy of a specific patient.

* * * * *